(12) United States Patent
Brandle

(10) Patent No.: US 6,255,557 B1
(45) Date of Patent: Jul. 3, 2001

(54) STEVIA REBAUDIANA WITH ALTERED STEVIOL GLYCOSIDE COMPOSITION

(75) Inventor: Jim Brandle, London (CA)

(73) Assignee: Her Majesty the Queen in right of Canada as represented by the Minister of Agriculture and Agri-Food Canada, London (CA)

( * ) Notice: Subject to any disclaimer, the term of this patent is extended or adjusted under 35 U.S.C. 154(b) by 0 days.

(21) Appl. No.: 09/220,592

(22) Filed: Dec. 28, 1998

Related U.S. Application Data

(60) Provisional application No. 60/080,175, filed on Mar. 31, 1998.

(51) Int. Cl.$^7$ .............................. A01H 5/00; A01H 5/10
(52) U.S. Cl. ..................... 800/263; 800/298; 800/260
(58) Field of Search .......................... 800/263, 260, 800/276, 270, 278, 298; Plt./373; 435/72, 74

(56) References Cited

U.S. PATENT DOCUMENTS

| | | | |
|---|---|---|---|
| P.P. 10,562 | 8/1998 | Sys et al. ........................ | Plt./373 |
| P.P. 10,563 | 8/1998 | Brandle et al. .................. | Plt./373 |
| P.P. 10,564 | 8/1998 | Marsolais et al. ............... | Plt./100 |
| 4,590,160 * | 5/1986 | Nishihashi et al. .............. | 435/78 |
| 6,031,157 | 2/2000 | Morita et al. .................... | 800/298 |

FOREIGN PATENT DOCUMENTS

| | | | |
|---|---|---|---|
| 51-131900 | 11/1976 | (JP) ............................. | C07H/1/080 |
| 54-030199 | 3/1979 | (JP) ............................. | C07G/3/00 |
| 54-30199 | 3/1979 | (JP) ............................. | C07G/3/00 |
| 54-41898 | 4/1979 | (JP) ............................. | A23L/1/221 |
| 55-111768 | 8/1980 | (JP) ............................. | A23L/1/22 |
| 56-121454 | 9/1981 | (JP) ............................. | A23L/1/22 |
| 59-45848 | 3/1984 | (JP) ............................. | A23L/1/22 |
| 62-960025 * | 5/1987 | (JP) ............................. | A01H/1/00 |
| 62-96025 | 5/1987 | (JP) ............................. | A01H/1/00 |
| 6-7108 | 1/1994 | (JP) ............................. | A23L/1/22 |
| 6-96025 | 4/1994 | (JP) ............................. | G06F/15/00 |
| 7-143860 | 6/1995 | (JP) ............................. | A23L/1/22 |
| 07143860 * | 6/1995 | (JP) ............................. | A23L/1/22 |

OTHER PUBLICATIONS

Chalapathi et al. Crop Research. vol. 14, No. 2, pp. 347–350, 1997.*
Hsu et al. Journal of Agricultural Researches. vol. 43, No. 1, pp. 29–38. (Translation provided), 1994.*
Shu. Scientia Agricultura Sinica, vol. 28, No. 2, pp. 37–42. (Translation provided), 1995.*
Lee, J. I., et al., New High Rebaudioside–A Stevia Variety "Suweon 11", Research Reports of the Office of Rural Development Crops, No. 24, 1982, pp. 186–188, XP002108478.

* cited by examiner

*Primary Examiner*—Paula Hutzell
*Assistant Examiner*—Melissa L. Kimball
(74) *Attorney, Agent, or Firm*—Oliff & Berridge, PLC

(57) ABSTRACT

This invention relates to Stevia plants characterized by exhibiting a high level of total glycosides, and a high ratio between rebaudioside A and stevioside. Preferably the Stevia plants comprise a level of total steviol glycoside of at least 14%, or of about 14.4% to about 18.8%, and the ratio of rebaudioside A:stevioside is of at least 9.1:1, or of about 9.3:1 to about 11.0:1. This invention also discloses a method for producing Stevia plants characterized in that the level of total steviol glycoside is at least of about 14%, and the ratio of rebaudioside A: stevioside is of at least about 9.1:1, comprising selecting at least two intermating genotypes of Stevia each comprising a ratio of rebaudioside A:stevioside of at least about 9:1:1, and a total steviol glycoside level of at least about 14%; allowing said at least two intermating genotypes to cross pollinate to produce a seed; collecting said seed; and growing said Stevia plant. Also disclosed are seeds and plants obtained from Stevia plants exhibiting high levels of total glycosides and high ratios between rebaudioside A to stevioside.

6 Claims, 5 Drawing Sheets

| | R | R1 |
|---|---|---|
| Rebaudioside A | β-Glc | β-Glc-β-Glc<br>       \|<br>     β-Glc |
| Stevioside | β-Glc | β-Glc-β-Glc |
| Rebaudioside C | β-Glc | β-Glc-β-Rha<br>       \|<br>     β-Glc |
| Dulcoside | β-Glc | β-Glc-β-Rha |

STEVIA REBAUDIANA WITH ALTERED STEVIOL GLYCOSIDE COMPOSITION

This application claims benefit of U.S. Provisional application Ser. No. 60/080,175, filed Mar. 31, 1998.

The present invention relates to a method of increasing the proportion of a desired steviol glycoside in Stevia. More specifically, this invention relates to increasing the levels of rebaudioside A within Stevia leaves.

BACKGROUND OF THE INVENTION

The worldwide demand for high potency sweeteners is increasing and, with blending of different sweeteners becoming a standard practice, the demand for alternatives is expected to increase. The sweet herb of Paraguay, *Stevia rebaudiana* Bertoni, produces an alternative sweetener with the added advantage that Stevia sweeteners are natural plant products. In addition, the sweet steviol glycosides have functional and sensory properties superior to those of many high potency sweeteners.

*Stevia rebaudiana* Bert. is one of 154 members of the genus Stevia and one of only two that produce sweet steviol glycosides. There is a large effort aimed at establishing Stevia as a crop in Japan as well as a number of other countries. However, no large scale mechanized production has been established and Stevia sweeteners are not yet found in mainstream food products in most countries of the world.

Stevia is a typical member of the Compositae. It is a small shrubby perennial growing up to 65 cm tall, and appears to be self-incompatible. The results of a complete diallel cross with 8 parents found the amount of selfing to range between 0 and 0.5%, while outcrossing ranged from 0.7 to 68.7%, indicating that some form of self-incompatibility system is operating (Katayama et al. 1976). Stevia is diploid and has 11 chromosomes, which is characteristic for most of the South American members of the genus.

The sweet diterpene glycosides of Stevia have been characterized and eight sweet glycosides of steviol have been identified. These glycosides accumulate in Stevia leaves where they may comprise from 10 to 20% of the leaf dry weight. On a dry weight basis, a typical profile for the four major glycosides found in the leaves of Stevia comprises 0.3% dulcoside, 0.6% rebaudioside C, 3.8% rebaudioside A and 9.1% stevioside. Other glycosides identified within Stevia include rebaudioside B, C, and E, and dulcosides A and B. Rebaudioside B may be an artifact formed from rebaudioside A during extraction since both rebaudioside A and rebaudioside D are found to convert to rebaudioside B by alkaline hydrolysis.

Of the four major diterpene glycoside sweeteners present in Stevia leaves only two, stevioside and rebaudioside A, have had their physical and sensory properties well characterized. Stevioside and rebaudioside A were tested for stability in carbonated beverages and found to be both heat and pH stable (Chang and Cook, 1983). Stevioside is between 110 and 270 times sweeter than sucrose, rebaudioside A between 150 and 320 times sweeter than sucrose, and rebaudioside C between 40 and 60 times sweeter than sucrose. Dulcoside A was 30 times sweeter than sucrose. Rebaudioside A was the least astringent, the least bitter, had the least persistent aftertaste and was judged to have the most favorable sensory attributes of the four major steviol glycosides (Phillips, 1989 and Tanaka, 1997). Dubois and Stephanson (1984) have also confirmed that rebaudioside A is less bitter than stevioside and demonstrated that the bitter notes in stevioside and rebaudioside A are an inherent property of the compounds and not necessarily the result of impurities in whole plant extracts. Bitterness tends to increase with concentration for both stevioside and rebaudioside A. Both stevioside and rebaudioside A are synergistic in mixtures with other high potency sweeteners such as aspartame and are good candidates for inclusion in blends (Schiffman et al. 1995).

Haga et al (JP 51-131900; 1976) disclose methods for the extraction of glycoside compounds from Stevia using a solvent, Ogawa (JP 55-111768; 1980) disclose methods involving the use of a solvent plus a decolorizing agent, Itagaki and Ito (JP 54-041898; 1979) disclose adsorption chromatography, Uneshi et al. (JP 54-030199; 1977) ion exchange, Matsushita and Kitahara (JP 56-121454; 1981) the selective precipitation of individual glycosides, and Tan and Ueki (JP 06-007108; 1994) teach methods based on ultra-filtration. Typical extraction processes involve aqueous or solvent extraction, followed by ion exchange, precipitation or coagulation with filtration, then crystallization and drying (Phillips 1989).

Plant breeding efforts in Stevia have been largely focused on improving leaf yield and rebaudioside A concentration in the leaves. Cultivar descriptions indicate that sufficient genetic variability exists to make significant genetic gains in leaf yield, rebaudioside A content and the ratio of rebaudioside A to stevioside (Brandle and Rosa 1992; Lee et al.1982; Shizhen 1995; Morita T JP 6-96025, 1987). Nakamura and Tamura (1985) report that the levels of dulcoside A and stevioside and rebaudioside A, and C are positively correlated with each other, while stevioside and rebaudioside A, and dulcoside and rebaudioside C are negatively correlated with each other. Total sweet glycoside concentration in some lines from China has been reported to be as high as 20.5%, and in separate cultivars rebaudioside A to stevioside ratios of 9:1 have been disclosed (Shizhen, 1995; Morita, 1987). But there have been no reports of plants comprising economically significant total steviol glycoside levels (i.e. from, or greater than, about 14%) combined with high ratios (i.e. from greater than about 9.1: 1) of rebaudioside A to stevioside. Such a raw material would permit conventional extraction methods, without the need for recrystalization of individual glycosides, to be used to produce a Stevia sweetener with more that 85% rebaudioside A.

Current propagation protocols of Stevia requires clonal propagation of plants comprising desired levels, and ratios, of sweeteners. A cultivar with a rebaudioside A to stevioside ratio of 0.96: 1, compared to 0.36:1 in the starting material, was developed with total glycosides of 22.4%. However, these plants, aside from having very low rebaudioside A to stevioside ratio, were self incompatible and could only be clonally propagated from cuttings (Lee et al. 1982). Other plants have been developed that exhibited rebaudioside A to stevioside ratio to levels as high as 9.1: 1, but total steviol glycosides were 10.1% (Morita T, JP 6-96025, 1987). Again due to self incompatibility the cultivar could not be reproduced using a seed based production system. The costs associated with clonal propagation limit the general applicability for large scale production of Stevia plants, especially in temperate North America where only annual production is an option.

Therefore, there is a need to develop a Stevia cultivar that is enriched in rebaudioside A, with high total steviol glycoside content and that can be produced using a relatively low cost method based on transplants produced from seed.

SUMMARY OF THE INVENTION

The present invention relates to a method of increasing the proportion of a desired steviol glycoside in Stevia, and plants comprising enhanced glycoside levels. More specifically, this invention relates to increasing the levels of rebaudioside A within Stevia leaves.

This invention provides a means of producing dried Stevia leaves that have high levels of total steviol glycosides and that are enriched in rebaudioside A, from Stevia plants produced from transplants grown from Stevia seed. The invention disclosed herein comprises a Stevia cultivar with high total glycoside levels and with a high proportion of rebaudioside A. The cultivar is designed to be higher in total steviol glycosides and rebaudioside A than current landrace or commercial plant material. It is preferred that the cultivar seed be produced from at least two intermating genotypes. The dried leaves are produced by growing plants from the seed, harvesting the plants and extracting the sweetener from the leaves.

According to the present invention there is provided a Stevia plant characterized in that the level of total steviol glycoside is at least of about 14%, and the ratio of rebaudioside A:stevioside is of at least about 9.1:1. Furthermore, this invention relates to a Stevia plant wherein said level of total steviol glycoside is of about 14.4 to about 18.8%, and the ratio of rebaudioside A:stevioside is of about 9.3:1 to about 11.0:1. This invention is also directed to a seed obtained from a Stevia plant as described above.

This invention also embraces a method (A) for producing a Stevia plant characterized in that the level of total steviol glycoside is at least of about 14%, and the ratio of rebaudioside A: stevioside is of at least about 9.1:1, comprising:
i) selecting at least two intermating genotypes of Stevia each characterized in that the ratio of rebaudioside A:stevioside is at least about 9.1:1, and a total steviol glycoside level is at least about 14%;
ii) allowing said at least two intermating genotypes to cross pollinate to produce a seed;
iii) collecting said seed; and
iv) growing said Stevia plant.

This invention also includes the method (A) described above wherein said at least two intermating genotypes are each characterized in that the level of total steviol glycoside is from about 14.4 to about 18.8%, or wherein said at least two intermating genotypes are each characterized in that the ratio of rebaudioside A: stevioside is from about 9.3:1 to about 11.0:1, or wherein said at least two intermating genotypes is each characterized in that the level of total steviol glycoside is from about 14.4 to about 18.8%, and a ratio of rebaudioside A: stevioside is from about 9.3:1 to about 15:1.

This invention is also directed to a plant produced by the method (A) as described above.

Furthermore, this invention provides for a method (B) of producing a natural sweetener characterized in being of about 150 to about 320 times sweeter than sucrose, comprising extracting said natural sweetener from a leaf of the Stevia plant of the present invention. This invention includes the method (B) as described wherein the sweetener is rebaudioside A, and wherein said step of extraction involves solvent extraction, ion exchange, precipitation, coagulation, crystallization, filtration, nanofiltration, supercritical fluid extraction, ultrafiltration, or a combination thereof.

This invention also embraces a first seed deposited with the ATCC, deposit number 203340 on Oct. 9, 1998, or a Stevia plant produced from this first seed. Furthermore this invention relates to a second seed derived from a Stevia plant, said Stevia plant produced from a first seed deposited with the ATCC, deposit number 203340 filed Oct. 9, 1998.

This invention also includes a Stevia plant obtained from a second seed as described above.

BRIEF DESCRIPTION OF THE DRAWINGS

These and other features of the invention will become more apparent from the following description in which reference is made to the appended drawings wherein.

DESCRIPTION OF PREFERRED EMBODIMENT

The present invention relates to a method of increasing the proportion of a desired steviol glycoside in Stevia. More specifically, this invention relates to increasing the levels of rebaudioside A within Stevia leaves.

Disclosed herein is the development of the components of a synthetic cultivar of Stevia characterized in having economically significant levels of glycoside along with a high ratio of rebaudioside A to stevioside. Also presented is the assembly of these components into a synthetic cultivar. As a result, this invention facilitates the low cost production of Stevia leaves that are used as the raw material for high potency sweeteners with high levels of rebaudioside A.

Steviol glycosides are diterpenoid natural products derived from the intermediate, geranylgeranyl pyrophosphate (GGPP) that lead to diterpenes. The initial steps leading to the steviol glycosides from GGPP are identical to those in gibberellin biosynthesis. Thus, GGPP is converted to ent-copalyl pyrophosphate (CPP) by CPP synthase and ent-kaurene is produced from CPP by ent-kaurene synthase. Subsequent oxidation of this product at the C-19 position to ent-kaurenoic acid is assumed to occur via the action of one or more P450 monooxygenases. At this point the pathways to the steviol glycosides and the gibberellins diverge. Steviol is produced by further hydroxylation of ent- kaurenoic acid at the C-13 position.

Figure 1:
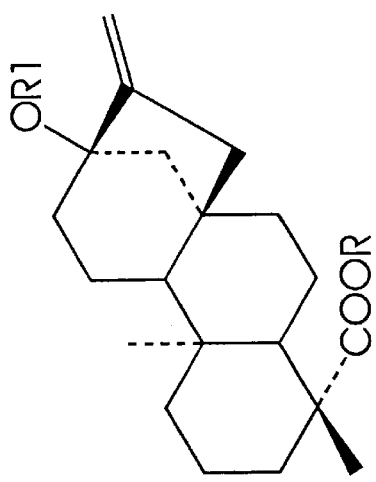
FIG. 1 shows the structures of the four major steviol glycosides
Figure 2A:
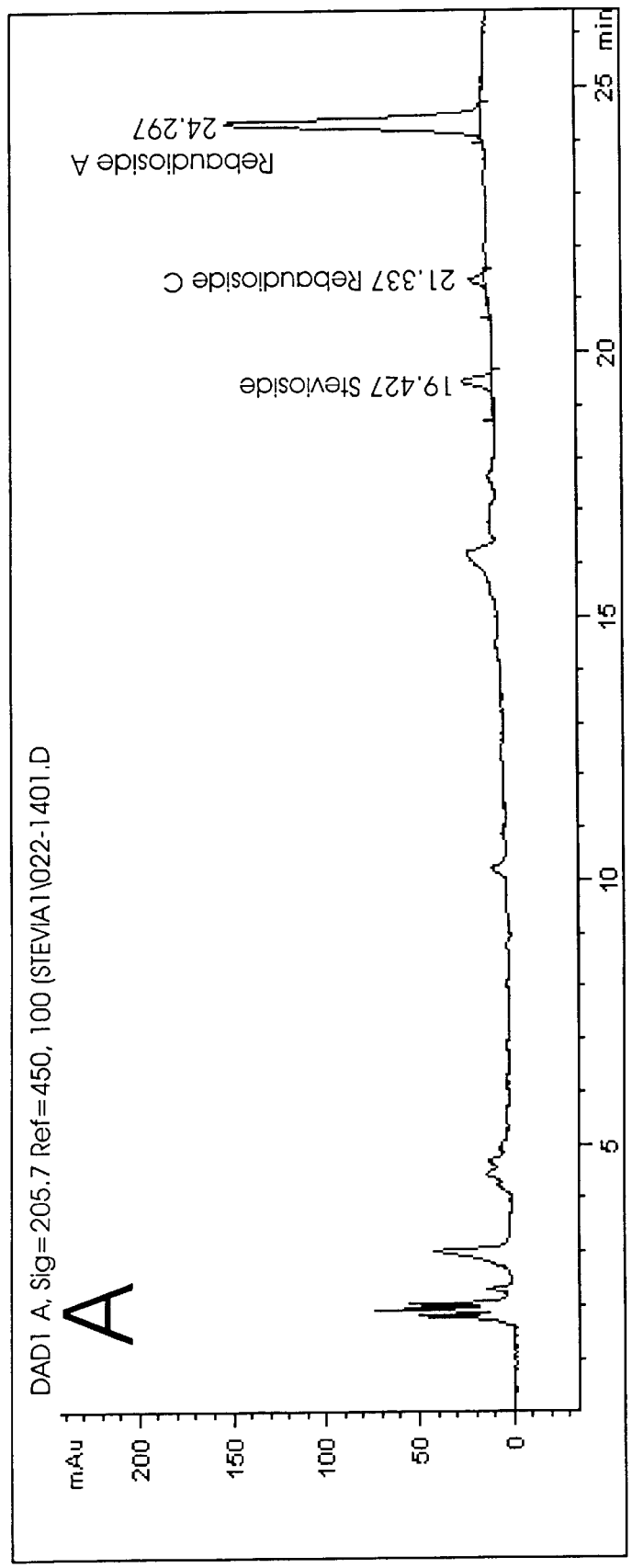
FIGS. 2a–2d show the chromatograms from high performance liquid chromatographic analysis of examples of clones A, B, C and D (see Table 1) used to assemble a synthetic Stevia cultivar.
Figure 2B:
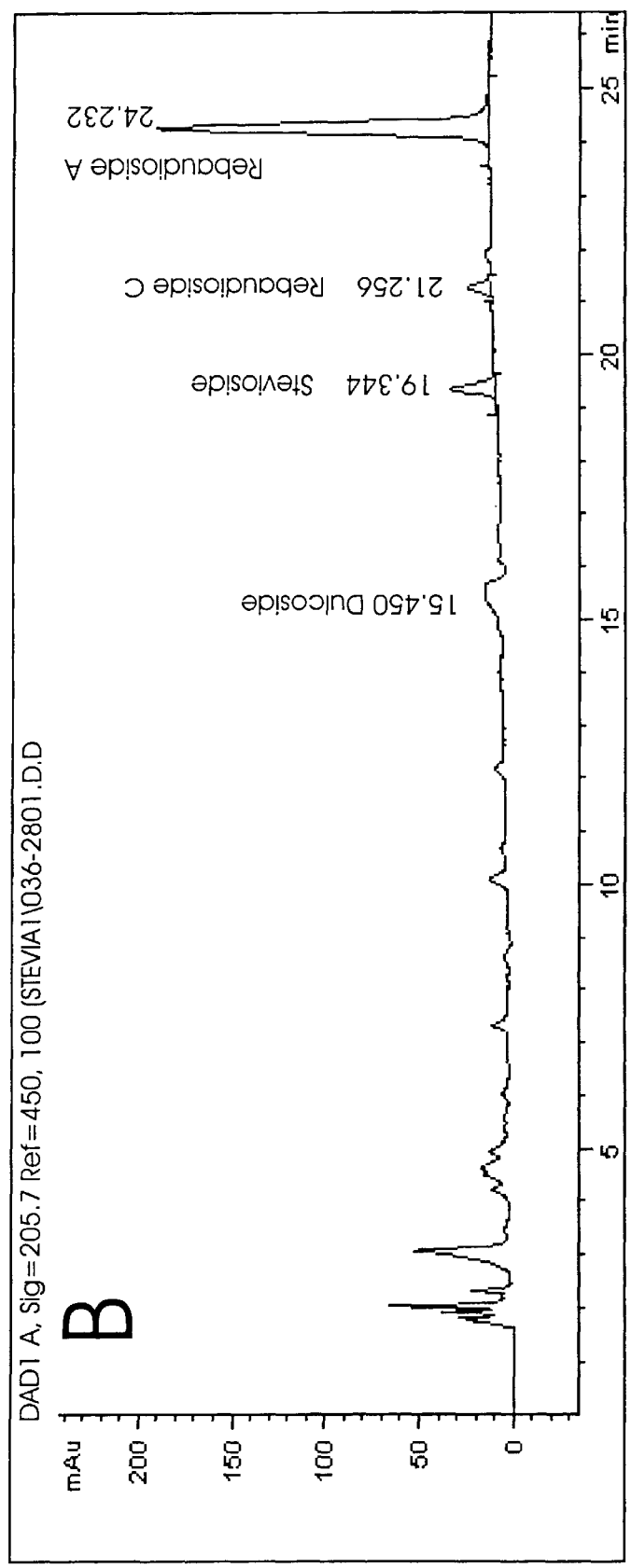
Figure 2C:
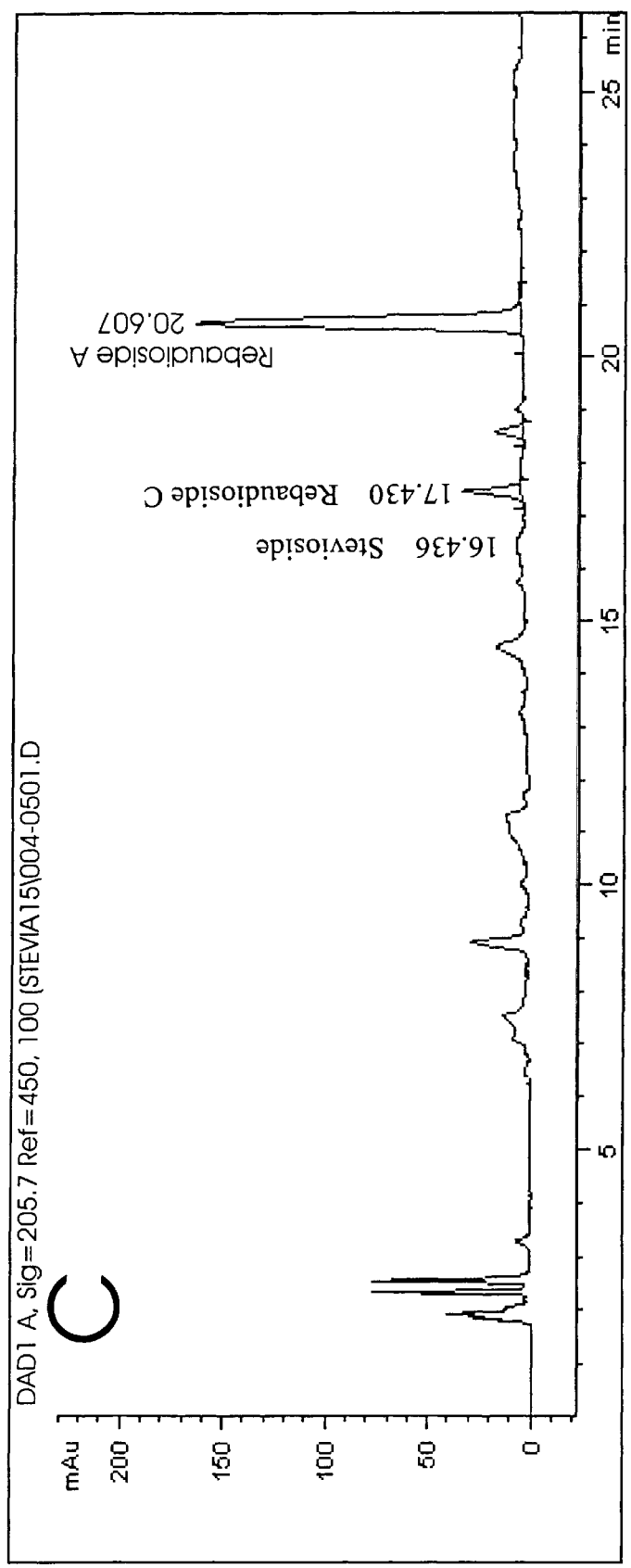
Figure 2D:
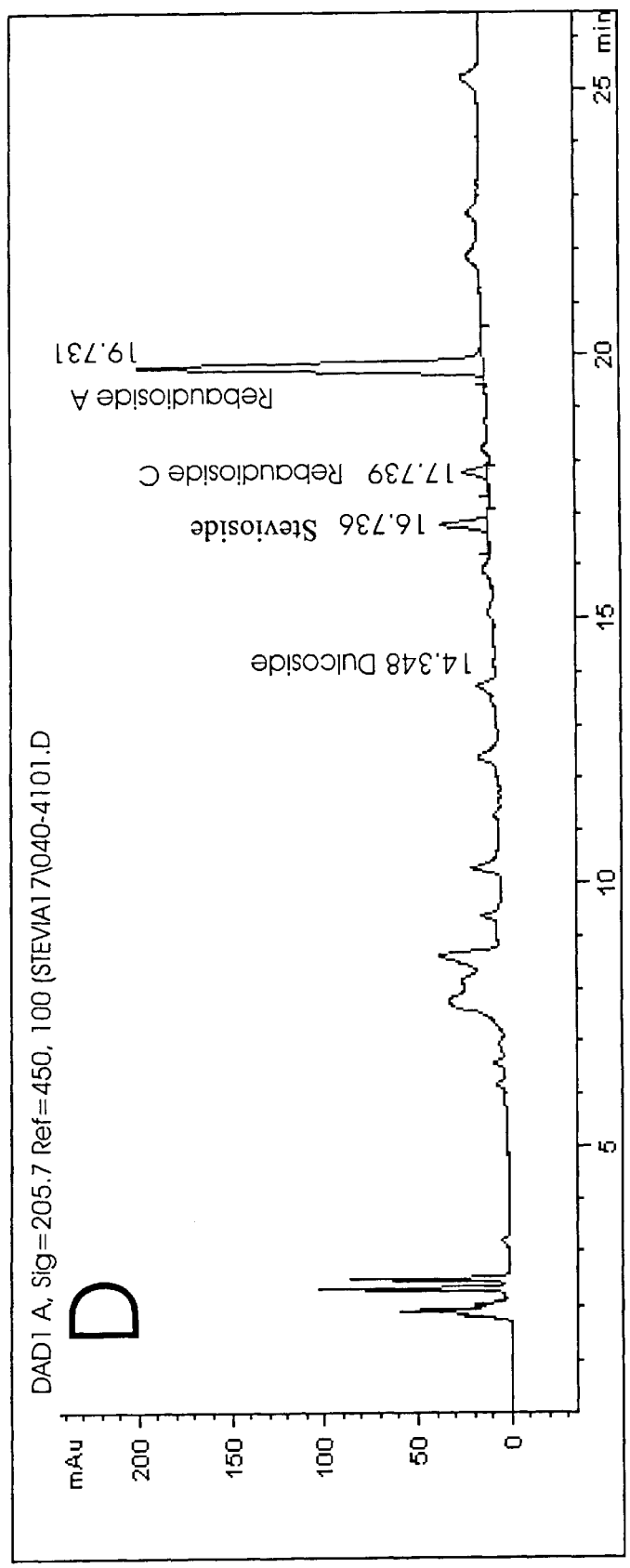

The two oxygenated functional groups of steviol, the C-19 carboxylate and the C-13 alcohol, provide attachment points for the sugar side chains that determine the identity of the 8 different glycosides identified to date. These glycan side chains are comprised predominately of glucose residues but may also contain rhamnose (FIG. 1).

On a dry weight basis, a typical profile for the four major glycosides found in the leaves of Stevia would be 0.3% dulcoside, 0.6% rebaudioside C, 3.8% rebaudioside A and 9.1% stevioside. Structures of these and other diterpenes and diterpene glucosides are presented in FIG. 1.

A wide range of analytical techniques have been employed to assess the distribution and level of sweet diterpenoid glycosides in S. rebaudiana. These include thin layer chromatography (Metivier and Viana 1979), over pressured layer chromatography (Fullas et al. 1989), droplet counter-current chromatography (Kinghorn et al. 1982), and capillary electrophoresis (Liu and Li 1995). Stevioside levels have also been determined enzymatically (Mizukami et al. 1982) and by near infrared reflectance spectroscopy (Nishiyama et al. 1992) in plant strains producing mainly stevioside. The most common analytical method, however, has been high performance liquid chromatography (Ahmed and Dobberstein 1982 a, b). Although separations have been achieved using silica gel, hydroxyapatite, hydrophilic, and size exclusion columns, amino bonded columns have been used most frequently for the analysis of the sweet glucosides.

By "leaf yield" it is meant the dry weight of Stevia leaves produced per unit area by a cultivar.

By "total glycosides" it is meant the amount on a dry weight basis of the four major steviol (ent-13-hydroxykaur-16-en-19-oic acid) glycosides synthesized in Stevia leaves. By economically significant total steviol glycoside levels, it is meant a total steviol glycoside levels of at least about 14% (on a dry weight basis). The ratio of rebaudioside A to stevioside (rebaudioside A:stevioside) refers to a value obtained by dividing the percentage, by weight, of rebaudioside A into the percentage, by weight, of stevioside found in the leaves of a selection or cultivar. The value is unit-less and can range from 0 to about 11.0. The term "high ratio" is used to refer to a ratio between rebaudioside A to stevioside of at least about 9.1:1.

A "synthetic" or "synthetic cultivar" refers to a Stevia cultivar produced by intercrossing clones or sibbed lines obtained from a breeding population during cycles of recurrent selection. To be considered a synthetic, there typically is more than one line or clone in the synthetic cultivar, the lines or clones are typically tested for combining ability, the lines or clones are typically preserved for future synthesis of the synthetic cultivar, and the lines or clones are typically combined by random crossing. Such synthetic cultivars are intended for use in crop production systems.

A breeding population refers to a group of plants created by sexual crossing of selected parents for the purpose of selection of novel genotypes.

A landrace cultivar is a one that is endemic to an area, consists of a mixture of morphological or chemotypes, but has unknown origins.

It is known in the art that plants producing Stevia leaves enriched in rebaudioside A are desirable compared with native Stevia or landrace cultivars low in rebaudioside A. However, such plants have in the past been not amenable to seed propagation. This invention resolves the problem of low total glycoside concentration in cultivars enriched in rebaudioside A and demonstrates a method of producing leaves high in total glycosides and enriched in rebaudioside A from seeds. The invention as disclosed herein is directed to obtaining plants that can be produced from seed based transplants from a synthetic Stevia cultivar and that exhibit economically significant total glycoside levels that are combined with high ratios of rebaudioside A to stevioside.

In order to create parents for the synthetic cultivar, crosses were made among a number of single plants and a large number of progeny planted out to the field and selections were made among those progeny. Leaves sampled from those selected plants were analyzed for glycoside concentration and composition using HPLC and selections that were high in glycosides and with rebaudioside A to stevioside ratios exceeding 9.1:1, and at least about 9.3:1. These selections were intercrossed in greenhouses during the winter and seed collected from the maternal parents. At the same time the cuttings were taken from the plants so that they could be used to duplicate the synthetic as required.

Seed from the maternal parents was retained as half sibs families and a portion bulked. The half sib families, the bulked sample and the parental clones were evaluated in a replicated field trial.

The plants so obtained are characterized in exhibiting high levels of total steviol glycosides and that are enriched in rebaudioside A. It is preferred that the cultivar seed be produced from at least two intermating genotypes. Each parent having ratios of rebaudioside A:stevioside of at least about 9.1:1. More specifically, the ratio may range from about 9.1:1 to about 11.0:1. Furthermore, each parent exhibits total steviol glycoside levels of at least about 14%. More specifically, the total steviol glycoside level may range from about 14.4 to about 18.8%. The production of seed of the cultivar is performed using standard technology known in the art. The dried leaves are produced by growing plants from the seed, harvesting the plants and extracting the sweetener from the leaves.

The present invention will be further illustrated in the following examples. However, it is to be understood that these examples are for illustrative purposes only, and should not be used to limit the scope of the present invention in any manner.

EXAMPLES

Selection of parental clones:

Sixty plants from 12 half-sib families (initial stock material obtained from Southern Crop Protection and Food Research Center, Agriculture and Agrifood Canada, Delhi Research Farm) were planted into a field that had been treated with methyl isothiocyantae/chloropicrin soil fumigant and fertilized with 34% N urea based fertilizer. Transplants were started in the spring of the same year in 288 plug trays filled with soilless potting mix and grown in a greenhouse at the Southern Crop Protection and Food Research Center, Delhi Research Farm (21 C, 16h daylength) until they were approximately 8 weeks old. They were transplanted and placed in rows 6 meters long and spaced 60 cm apart with 20 cm between plants. Plants were allowed to grow through the summer and received one supplemental irrigation through the season. Twenty plants from each half-sib family were selected in the field and approximately 5 g of leaves sampled for analysis. Sampling points were equally distributed through the plant and leaves were sampled from the lower, mid and top portions of the selected plants. Leaves were then frozen at −70C and then lyophillized. Leaf tissue was placed in a lyophillizer for five days then ground with a Wiley mill until the tissue passed through a 40 mesh screen.

Isolation of glycosides from Stevia leaves

Glycosides may be obtained from harvested leaves using a variety of methods known within the art, for example solvent extraction (Haga et al, JP 51-131900; 1976), solvent extraction along with a decolorizing agent (Ogawa, JP 55-111768; 1980), adsorption chromatography (Itagaki and Ito, JP 54-041898; 1979), ion exchange chromatography (Matsushita and Kitahara, JP 56-121454; 1981), selective precipitation of individual glycosides, or ultra-filtration (Tan and Ueki, JP 06-007108; 1994). Other methods may include nanofiltration, super critical fluid extraction etc, as would be evident to one of skill in the art. Typical extraction processes involve aqueous or solvent extraction, followed by ion exchange, precipitation or coagulation with filtration, then crystallization and drying.

Sample Analysis

Three hundred milligrams of plant material were weighed into a 15 mL polypropylene centrifuge tube and 10 mL of 1:1 (v/v) acetonitrile-water were added to the tube. The tubes containing the samples were placed in an ultrasonic bath, set at maximum ultrasonification, for 15 minutes. The sample tubes were stirred occasionally and rotated in the bath to ensure uniform extraction of steviol glycosides. The sample tubes were then centrifuged for 15 minutes at 1500 rpm and then the supernatant transferred to a 10 mL volumetric flask and the volume made up with acetonitrile. The samples were then filtered through a 45 micron filter and a Waters $NH_2$ Sep-Pak® cartridge to remove contaminants and coeluting compounds. Stevioside was used as the standard in all analyses. The response factor for stevioside was corrected and used for rebaudioside A, rebaudioside C and dulcoside.

A Waters carbohydrate cartridge column with a propylamine bonded phase, is typically used to analyze the diterpenoid glycosides in a large number of S. rebaudiana leaf samples.

All analysis were performed on a Hewlett-Packard 1090 liquid chromatograph equipped with a three channel solvent delivery system and autosampler and a diode array detector (205 nm) interfaced with a chem work station. Separation of the four major steviol glycosides was with a 250×4.6 mm i.d. Waters cartridge carbohydrate column, the guard column was a carbohydrate sentry column and the gradient water-acetonitrile. The flow rate was 1.5 mL/min and the solvents were water (pH 5.25), acetonitrile and acetonitrile. The retention times were: 14.5 min. for dulcoside, 18.8 min. for stevioside, 20.4 min. for rebaudioside C and 23.5 min. for rebaudioside A (see FIGS. 2a–2d). The steviol glycosides in the samples were identified by their retention times, there concentration calculated by an external standards method and they were reported on a dry weight basis.

As a result of this screening process, four plants were selected that exhibited high ratios of rebaudioside A to stevioside of at least 9.1: 1, and that also comprised a level of total steviol glycosides of at least about 14.%. These plants are denoted as A to D in Table 1. Also shown in Table 1 is a comparison of glycoside compositions of the plants A–D, the 13 half-sib families (Family) and a landrace cultivar (Brazil). Brazil exhibits a moderate level of total glycoside, however, the rebaudioside A:stevioside ratio is low. Similarly, high levels of total glycosides are detected in the half-sib family, yet the rebaudioside A:stevioside ratio is low. However, Stevia plants A-D each exhibit economically significant total glycoside levels, and a high ratio between rebaudioside A to stevioside.

m×1 m insect cage screened with 10 mm mesh and allowed to regrow under 12 h daylength at an air temperature of 21° C. Immediately following the appearance of the first open flowers a hive of bumble bees was introduced into the insect cage and the bees allowed to forage the flowers to promote intercrossing. Seed was collected from each of the plants after three weeks and regularly for 8 weeks thereafter. The bulked seed was given the cultivar name AC Blackbird. This seed was also deposited with the ATCC, 10801 University Blvd., Manassas VA, 20110-2209 U.S.A., with deposit number, 203340 on Oct. 9, 1998.

Production of Seedlings for Transplantation

Seed from each of the four selected plants and a bulk of that seed was planted one seed at a time in 288 cell plug trays, with a plug depth of 4.4 cm. Cuttings from each of the parental clones were started two weeks later by taking shoot tip cuttings placing each cutting in a plug tray cell and watering regularly until roots were established. The trays were filled with soil-less potting mix, and in the case of the seed trays, were watered up to three times daily until the seed had germinated and the seedlings were established. Following seedling and cutting establishment the trays were watered two times per day and fertilized every ten days with 20-20-20 until ready for the field.

Evaluation of Synthetic Cultivar Performance

An experiment was designed to compare the glycoside composition of the synthetic cultivar AC Blackbird to the four half-sib families and clonally propagated copies of the original selections. The experiment employed a randomized complete block design and had 11 treatments. Each plot contained 8 plants. Seedlings and transplants were started in 200 plug trays in early spring. The experiment was planted about seven weeks later and leaves were sampled for HPLC analysis 5 months after the initial seedlings were started. Production conditions were those used for the selection of the parental clones and outlined previously. The glycoside analysis method was that used for the parental clones and detailed previously. Total steviol glycoside levels of least

TABLE 1

Concentrations of the four major glycosides, total glycoside concentration and the ratio of rebaudioside A to stevioside and their standard deviation (in brackets) in the a landrace cultivar from Brazil (Brazil), 13 half-sib families (Family), and the four selections used to make up AC Blackbird (A, B, C and D)

| | | | % | | | |
|---|---|---|---|---|---|---|
| Selection | Dulcoside | Stevioside | Rebaudioside C | Rebaudioside A | Total | Reb A: Stev ratio |
| Brazil[1] | 0.42(0.3) | 9.10(2.2) | 0.85(0.4) | 3.54(2.0) | 13.90(2.0) | 0.65(0.4) |
| Family[2] | 0.12(0.2) | 4.44(1.8) | 1.29(0.2) | 14.43(2.1) | 20.28(2.7) | 3.92(2.0) |
| A | 0.00 | 1.13 | 0.81 | 12.47 | 14.41 | 11.00 |
| B | 0.21 | 1.68 | 1.10 | 15.78 | 18.76 | 9.39 |
| C | 0.00 | 1.54 | 0.83 | 14.25 | 16.66 | 9.30 |
| D | 0.02 | 1.34 | 0.99 | 13.55 | 15.90 | 10.10 |

[1]Brazil represents a landrace cultivar from Southern Brazil and the values are the average of 50 observations
[2]Family represents all of the selections made within the 13 half-sib families and the values are the average of 255 observations Sexual Crossing of Selected Clones To Create AC Blackbird Plants A, B, C and D (Table 1) were isolated from the field in the fall, transplanted in 20 cm pots, and the existing vegetative growth trimmed back to the crown. These plants were placed on a raised bench in a greenhouse inside of a 1.3 about 14% were observed in all of the clonally propagated parents, in 3 of 4 half sibs and in the synthetic cultivar AC Blackbird. A ratio of rebaudioside A to stevioside of at least about 9.1:1 was observed in three of four clonally propagated parents, two of three half sibs and in AC Blackbird.

TABLE 2

Concentration (w/w %) of the four major steviol glycosides, total glycoside concentration and the ratio of rebaudioside A to stevioside in a landrace cultivar from Brazil (Brazil) a locally adapted selection (SR5), clones A, B, C and D, half-sib families (HS-A, B, C, D) resulting from intercrossing the clones and a bulk synthetic (AC Blackbird) from leaves sampled from a trial grown at the Delhi Research Station

| Entry | Dulco-side | Stevio-side | Rebaudio-side C | Rebaudio-side A | Total | Ratio |
|---|---|---|---|---|---|---|
| | (w/w %) | | | | | |
| Brazil | 0.48 | 7.93 | 0.65 | 4.10 | 13.16 | 0.52 |
| SR5 | 0.83 | 13.32 | 0.37 | 1.72 | 16.26 | 0.13 |
| A | 0.03 | 0.71 | 0.89 | 11.55 | 13.19 | 15.56 |
| B | 0.00 | 1.29 | 1.06 | 14.88 | 17.23 | 11.64 |
| C | 0.00 | 1.50 | 1.38 | 14.94 | 17.98 | 10.17 |
| D | 0.16 | 1.40 | 1.15 | 12.25 | 14.80 | 8.83 |
| HS-A | 0.01 | 0.83 | 0.69 | 9.31 | 10.84 | 11.26 |
| HS-B | 0.01 | 1.78 | 1.04 | 12.39 | 15.23 | 6.94 |
| HS-C | 0.03 | 1.37 | 1.26 | 12.77 | 15.41 | 10.01 |
| HS-D | 0.01 | 2.38 | 1.11 | 12.38 | 16.34 | 6.19 |
| AC BLACKBIRD | 0.03 | 1.27 | 1.27 | 12.49 | 15.06 | 9.96 |
| Standard Error ± | 0.1 | 0.2 | 0.2 | 0.6 | 0.7 | 1.0 |

The present invention has been described with regard to preferred embodiments. However, it will be obvious to persons skilled in the art that a number of variations and modifications can be made without departing from the scope of the invention as described herein.

REFERENCES

Ahmed, M. S. and Dobberstein, R. H. 1982a. *Stevia rebaudiana*. II. High-performance liquid chromatographic separation and quantitation of stevioside, rebaudioside A and rebaudioside C. J. Chromatogr. 236: 523–526.

Ahmed, M. S. and Dobberstein, R. H. 1982b. *Stevia rebaudiana*. III. High-performance liquid chromatographic separation and quantitation of rebaudiosides B, D, and E, dulcoside A, and steviolbioside. J. Chromatogr. 245: 373–376.

Brandle, J. E., and Rosa, N. 1992. Heritability for yield, leaf:stem ratio and stevioside content estimated from a landrace cultivar of *Stevia rebaudiana*. Can. J. Plant Sci. 72: 1263–1266.

Chang, S. S. and Cook, J. M. 1983. Stability studies of stevioside and rebaudioside A in carbonated beverages. J. Agric. Food Chem. 31: 409–412.

DuBois, G. E. and Stephenson, R. A. 1984. Diterpenoid sweeteners. Synthesis and sensory evaluation of stevioside analogues with improved organoleptic properties. J. Med. Chem 28:93–98.

Fullas F., Kim J., Compadre C. M., Kinghorn A. D. 1989 Separation of natural product sweetners using over-pressured layer chromatography. J. Chrom. 464:213–219.

Katayama O., Sumida, T, Hayashi, H. and Mitsuhashi H. 1976. The practical application of Stevia and research and development data (English translation). I.S.U. Company, Japan. 747 pp.

Kinghorn, A. D., Nanayakkara, N. P. D., Soejarto, D. D., Medon, P. J. and Kamath, S. 1982. Potential sweetening agents of plant origin. I. Purification of *Stevia rebaudiana* sweet constituents by droplet counter-current chromatography. J. Chromatogr. 237: 478–483.

Lee, J. I., Kang, K. H., Park, H. W., and Ham, Y. S. 1982. New high rebaudioside—A stevia variety "Suweon 11" (English abstr.). Res. Rep. ORD 24: 186–188.

Liu, J. and Li, S. F. Y. 1995. Separation and determination of Stevia sweeteners by capillary electrophoresis and high performance liquid chromatography. J. Liq. Chromatogr. 18: 1703–1719.

Matsushita, K., and Kitahara, T. 1981 Separation of stevioside and rebaudioside A by crystallization (English abstr.). Jap. Patent 56–121454.

Mauri, P., Catalano, G., Gardana, C. and Pietta, P. 1996. Analysis of Stevia glycosides by capillary electrophoresis. Electrophoresis 17: 367–371.

Metivier, J. and Viana, A. M. 1979. Determination of microgram quantities of stevioside from leaves of *Stevia rebaudiana* Bert. by two-dimensional thin layer chromatography. J. Exp. Bot. 30: 805–810.

Mizukami, H., Shiiba, K. and Ohashi, H. 1982. Enzymatic determination of stevioside in *Stevia rebaudiana*. Phytochemistry 21: 1927–1930.

Nakamura, S. and Tamura, Y. 1985. Variations in the main glycosides of stevia. Jap. J. Trop. Agric. 29:109–115.

Nikolova-Damyanova, B., Bankova, V. and Popov, S. 1994. Separation and quantitation of stevioside and rebaudioside A in plant extracts by normal-phase high performance liquid chromatography and thin-layer chromatography: a comparison. Phytochem. Anal. 5: 81–85.

Nishiyama, P., Alvarez, M. and Vieira, L. G. E. 1992. Quantitative analysis of stevioside in the leaves of *Stevia rebaudiana* by near infrared reflectance spectroscopy. J. Sci. Food Agric. 59: 277–281.

Phillips, K. C. 1989. Stevia: steps in developing a new sweetener. Pages 1–43 in T. H. Grenby ed. Developments in sweeteners, Volume 3. Elsevier Applied Science, London.

Schiffman, S. S., Booth, B. J., Carr, B. T., Losee, M. L., Sattely-Miller, E., and Graham, B. G. 1995. Investigation of synergism in binary mixtures of sweeteners. Brain Res. Bull. 38: 105–120.

Shizhen, S. 1995. A study on good variety selection in Stevia rebaudiana Scientia Agricultura Sinica 28: 37–41.

Sumida, T. 1968. Reports on *Stevia rebaudiana* Bertoni M. introduced from Brazil as a new sweetness resource in Japan. Misc. Pub. Hokkaido Natl. Exp. Sta. 2: 69–83.

Tanaka, O. 1987. Improvement of taste of natural sweetners. Pure Appl. Chem 69:675–683.

The embodiments of the invention in which an exclusive property of privilege is claimed are defined as follows:

1. A *Stevia rebaudiana* Bertoni plant characterized in that the level of total steviol glycoside is at least of about 14% of leaf dry weight, and the ratio of rebaudioside A:stevioside is of at least about 9.1:1, wherein said plant is the cultivar AC Blackbird, seeds of which have been deposited with ATCC under accession number 203340.

2. A seed obtained from said Stevia plant of claim 1.

3. A *Stevia rebaudiana* Bertoni plant characterized in that the leaf concentration of rebaudioside A is greater than 124 grams per kilogram of leaf tissue, and is about 82% of the total glycosides; wherein said plant is a seed-based cultivar, wherein said plant is the cultivar AC Blackbird, seeds of which have been deposited with ATCC under accession number 203340.

4. A seed obtained from the Stevia plant of claim 3.

5. A plant grown from a seed according to claim 4.

6. A plant grown from a seed according to claim 2.

* * * * *